US00PP20978P3

(12) United States Plant Patent
Benardella

(10) Patent No.: US PP20,978 P3
(45) Date of Patent: May 4, 2010

(54) ROSE PLANT NAMED 'BENOCHO'

(50) Latin Name: *Rosa hybrida*
Varietal Denomination: BENocho

(75) Inventor: Frank Benardella, Millstone Township, NJ (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 0 days.

(21) Appl. No.: 12/286,998

(22) Filed: Oct. 3, 2008

(65) Prior Publication Data

US 2010/0088790 P1 Apr. 8, 2010

(51) Int. Cl.
*A01H 5/00* (2006.01)

(52) U.S. Cl. ..... Plt./131

(58) Field of Classification Search ..... Plt./131
See application file for complete search history.

*Primary Examiner*—Susan B McCormick Ewoldt

(57) ABSTRACT

This new rose plant is of a medium size and upright growing habit. It bears hybrid tea-form, white flowers with red margins, primarily one to a stem. The upper surface of those flowers may become entirely flushed with a deep red depending on the intensity of the sun. The plant makes an excellent decoration in the garden.

1 Drawing Sheet

Genus and species: *Rosa hybrida.*
Varietal denomination: 'BENocho'.

BACKGROUND OF THE INVENTION

The present invention relates to a new and distinct variety of hardy, bush-type rose plant. This new variety is from a single seedling originated by Frank A. Benardella under controlled conditions in a greenhouse in Millstone Township (formerly Englishtown), N.J., by crossing the following two rose plants: The seed parent is a medium pink miniature rose, 'BENminn' (U.S. Plant Pat. No. 14,894). The pollen parent is a red hybrid tea, 'JACecond', (U.S. Plant Pat. No. 11,369). The new rose was given the code name of 'BENocho'.

The primary goal of this breeding program is to produce unique roses with award winning, hybrid tea form on plants having favorable attributes that will increase public appeal. To achieve this goal roses are selected for this hybridizing program primarily for their award winning, hybrid tea form. Pertaining to this particular cross, both parents have been noted for their exhibition form flowers that are often borne one to a stem. Both are traits visible in this new invention.

SUMMARY OF THE INVENTION

The present invention relates to a new and distinct variety of hardy, bush-type rose plant primarily characterized by the bright red border on the white petals of its hybrid-tea form flowers, which are borne on an upright bush growing two to three feet tall.

It is easily distinguished from its parents. The new invention and its parents all have hybrid-tea type, exhibition form flowers. On the new invention and the pollen parent, 'JACecond', flowers are borne primarily singly and have similar petal counts. The most obvious differences with the pollen parent are in the size and coloring of those flowers as well as the plant size. Averaging four inches across, the open blooms on 'JACecond' are at least an inch larger than the largest open blooms on 'BENocho'. The flowers on 'JACecond' are a solid red and on 'BENocho' they are white edged with red. 'JACecond' can grow up to five feet tall and four feet wide in its first year while 'BENocho' can reach a mature height of two to three feet and a width of up to two and a half feet in three to five years. The seed parent in this cross, 'BENminn', is a miniature rose of about the same height as this new invention but with flowers of a solid medium-pink that are ½ to 1¼ inches smaller in diameter and with slightly fewer petals.

The pollen parent for this new invention, 'JACecond', has been used in several other successful crosses in this same breeding program. From those crosses, perhaps the one most closely resembling this new invention in plant habit and flower form is 'BENpete', not patented. (Information about 'BENpete' is available on the HelpMeFind website.) Both 'BENpete' and this new invention, 'BENocho', have hybrid tea-type, exhibition form flowers, borne on upright growing plants of similar habit, though 'BENpete' may be a little more compact. The new invention has white flowers with red margins and is flushed with red depending on the intensity of the sun. 'BENpete' has predominately red flowers with the base and reverse of the petals being white.

The field of comparison with other red and white flowering roses may be narrowed down to those with hybrid-tea type form flowers with red margins on white petals. This new variety is differentiated from other red and white flowering roses with hybrid tea, exhibition-type blooms by its very white flower-petals edged in red and the manner wherein they become heavily flushed with red on the upper surface, when grown in full sun, and also by its very upright plant habit. The variety is further characterized by:

- Flowers that remain high centered throughout their life.
- Upper petal surfaces are satiny except along the red margin where they are velvety.
- The shape of the flower petals is rounded to oblate.
- Flowers do not self-pollinate.
- The flower has moderate fragrance.
- The plant is uniformly branched and has dark green, semi-glossy foliage.

This new invention grows and blooms satisfactorily both in the greenhouse and outdoors.

This new invention can serve as a bright decoration in the garden as a perennial or in large containers.

Asexual reproduction by cuttings of this new variety in Millstone Township, N.J., and Arroyo Grande, Calif., show that all distinguishing characteristics of this rose continually come true to form.

BRIEF DESCRIPTION OF THE DRAWING

There are three separate images in the accompanying drawing, depicted in color as nearly correct as it is possible to make in a color illustration of the character.

The largest is a photograph taken at dusk in mid-September of a two to three year old plant of this new invention, growing outdoors, in the ground, in Essex County, Mass. Buds, flowers, stems, prickles and foliage of this new variety in different stages of development are visible on this plant. This image most resembles the botanical description that follows.

In the lower left-hand corner is a close-up image of flowers from a plant grown in a glass-covered greenhouse in Millstone Township, N.J.

In the lower right-hand corner is an image, taken in August, of a bucket of flowers cut from plants grown in a plastic covered greenhouse in Arroyo Grande, Calif.

BOTANICAL DESCRIPTION OF THE PLANT

The following observations, measurements, values and comparisons are from a five year old plant of *Rosa hybrida,* 'BENocho', grown in a 12 inch plastic nursery container in artificial soil mix, outdoors in Ipswich, Mass., from May through September, 2008, unless otherwise noted. Fertilization was erratic. Phenotypic expression varies with environmental, cultural and climatic conditions. Color References are made using The Royal Horticultural Society Colour Chart, except where common terms of color are used.

FLOWERS

Blooming Habit: 'BENocho' is a repeat blooming rose bush with flowers borne on slightly crooked, strong stems, mostly singly but also in small, loose clusters of 2 to 4. From the point when sepals begin to divide until the flower starts to fade was between 20 and 25 days. When borne singly, flowering side shoots may grow from nodes immediately below the bloom, beginning their growth in the spring and early summer as the top bud begins to unfurl, and in late summer and early fall after the flower fades. The complete cycle repeats every 32 to 40 days, in season, but may appear to be near constantly in bloom because of the flowering side shoots. The removal of open and spent flowers from below the first leaf-node does hasten the time of production of the next blooms.

Bud form is ovate, slightly rounded at the base and with an acute apex. Buds generally have a diameter of $^{15}/_{32}$ inch, but have been measured up to $^{19}/_{32}$ inch in diameter when greenhouse grown. The height of the bud varies from $^{22}/_{32}$ to $^{27}/_{32}$ inch and may be $^{29}/_{32}$ inch tall when greenhouse grown.

Sepals: The flower has five sepals, permanently attached to the receptacle, extending $^{14}/_{32}$ inch beyond the tip of the bud just before the sepals divide. Outer surfaces are semi-glossy at the base with the rest of the surface being matte. Inside surfaces have a fine pubescent covering. The outer sepals are a darker yellow-green than the inner sepals. The color of the outer surfaces of the outer sepals is a medium to dark yellow-green, near 146A, with lighter yellow-green, near 146D, in the basal area and forming a narrow, acute triangle up through the center of the sepal. The inside surface is a dark yellow-green, near 147B, along the margins and a lighter yellow-green, near 144C, in the center and up through the center. The color of the outer surface of the inner sepals is a medium yellow-green, between 144B and 137C, with the basal area and triangular area up through the center being lighter, near 146B. The inside surface is a medium yellow-green, between 146A and 137B, with the basal area and up through the center being lighter, near 144B. Outer surfaces of all sepals may be flushed with a deep purple-red, near 174A and are peppered with stipitate glands in varying amounts, from few to many; when there are many, they appear to be arranged in straight and near parallel lines. The outer surfaces of the inner sepals become puberulent approaching the apex and margins, which are heavily ciliated. The margins of the outer sepals are lined with stipitate glands, including along any foliar appendages. Sepals unfold ahead of the petals to a point anywhere between near an 80° angle to the receptacle and near parallel to the receptacle. They remain attached to the receptacle and may return to perpendicular to the receptacle or may remain in their recurved position after the petals drop. They dry with the receptacle and peduncle.

The general shape of the individual sepals is ovate-lanceolate. The two outer sepals have lanceolate apices and one to three foliar appendages along each margin. On full open flowers when borne singly, the width of these two outer sepals is usually $^{12}/_{32}$ inch with a length averaging $1^{12}/_{32}$ inches, varying from $1^{6}/_{32}$ to $1^{24}/_{32}$ inches. The two innermost sepals have acuminate apices. Their width is also usually $^{12}/_{32}$ inch but ranges from $^{9}/_{32}$ to $^{13}/_{32}$ inch, and their length ranges from $1^{1}/_{32}$ to $1^{10}/_{32}$ inches. There are usually no foliar appendages on these inner sepals but on rare occasions there may be a curvilineal appendage along one margin. The one sepal in-between the inner and outer sepals displays characteristics of both the inner and outer sepals, including the coloring, dividing down the center. The width varies between $^{11}/_{32}$ and $^{13}/_{32}$ inch. The length ranges from $1^{7}/_{32}$ to $1^{15}/_{32}$ inches. The sepals on flowers borne in clusters may be of the same width but are generally shorter by about one-third, even when the sizes of the open blooms are the same.

The receptacle is obovate, truncated at the top, and the base is tapered to connect evenly to the peduncle. The surface is glossy and pilose. On full open flowers, the diameter at its widest point was most often measured at $^{9}/_{32}$ inch, varying from $^{9}/_{32}$ to $^{13}/_{32}$ . The height was most often $^{12}/_{32}$ inch, varying from $^{12}/_{32}$ to $^{15}/_{32}$ inch. The color is a medium yellow-green, between 144A and 144B.

Bloom size when borne singly and fully expanded often reaches up to 3 inches in diameter with a profile depth of $1^{22}/_{32}$ inches. Secondary blooms vary in size from $2^{3}/_{32}$ to $2^{12}/_{32}$ inches in diameter and $^{26}/_{32}$ to $^{31}/_{32}$ inch deep. Blooms open high-centered and remain high centered throughout, developing a convex upper profile. The lower profile progresses from convex to flattened-concave. Petal counts have been noted from 19 to 30 with 3 to 5 petaloids. Fragrance is moderate.

Petals are moderately thick. The upper surface is smooth and satiny becoming velvety toward the margin where the color becomes red. The lower surface is satiny. The main central vein, from the point of attachment to the apex, the primary lateral veins originating from it, and to a lesser degree the secondary lateral veins protrude significantly on the reverse of the outer petals and to a much lesser degree on the inner petals. The five outer petals are oblate with a broadly obtuse base. On the full open flower, the petals have been measured between 1 13/32 to 1 22/32 inches wide and with a length of 1 9/32 to 1 13/32 inches long. The petals are always wider than they are long by 4/32 to 9/32 inch and no two petals on a flower being the same. The outer margins are rounded and have been observed as entire in August, and with an acute apex with a small indentation on each side of the apex on Greenhouse grown plants in May. Intermediate petals are nearly round with an obtuse base and margins observed similar to those of the outer petals. Inner petals are obovoid with a funnel-shaped base. They have been observed with a broad, angular shaped margin in August and with an ovate margin with an acute apex on the greenhouse grown plants in May. Petal edges recurve slightly.

Color intensity on the flowers is very dependent on the intensity of the light while they are forming. When grown in full sunlight, the entire petals become flushed with red. In filtered light or partial shade, the red coloring is more limited to the area near and along the outer margins. The following observations were taken from a plant grown in a container, in full sun, June through September, in Essex County, Mass., except where otherwise noted.

When the sepals first divide, the colors seen are a very dark red-purple, near 187A, usually becoming near 59B, Indian Lake Red, as it proceeds down or out into the white, closest to 155D, of the petal; and as the white areas become exposed to the sun, they become flushed or mottled with a Cardinal Red, near 53A. During the first few days, the color along the outer margin on the upper surface of the petals appears a deep red, between 46B and 58B, which becomes dispersed into the white of the petal. The basal area is a very light Primrose Yellow, near 4D and the point of attachment is near 4C. On the reverse, the margins are near 57B, Rose Bengal. The rest of the petal is a white, near 155D; areas that had been a dark red-purple when the sepals first divided have become a Ruby Red, near 59A, or a bit lighter, between 59A and 53A, or a combination of both colors. There may be other areas and streaks on the reverse of the petals of a medium red, near 53D, or a color between 53D and 57B, or a combination of both colors. The basal area is near 4D and may have splashes of a Neyron Rose, near 55B. The point of attachment is near 154D, a very light yellow-green. Color intensifies toward the center of the bloom. The inner petals near the center of the flower are a darker red along the margins, between 46A and 53A, and becoming near 53C as it blends down toward the basal area, which is near 155D. The point of attachment is also slightly darker on the inner petals, a Primrose Yellow, near 4B. The reverse of the inner petals is a yellow-white, near 158D. Their margins are darker than those on the reverse of the outer petals, being a combination of near 59B and near 53A. This color disperses downward into the petal becoming lighter as it proceeds away from the margin. The basal area is 158D and the point of attachment is near 4C.

When the flower is half open, the color along the margins on the upper surface of all petals has lightened a bit to a color between 57A and 46B which disperses into the white, near 155D, of the petals. Basal areas are near 4D, except on the inner petals where it is near 155D. The points of attachment are near 4D. Progressing toward the center of the flower, the area of red widens gradually in each successive row of petals. The reverse of the petals is near 4D with near 57A along the margins and blending downward into the near 4D. Progressing toward the center of the flower, the red coloring on the reverse darkens and the area along the margins widens a bit, into a band about 1/8 inch wide. The basal area is near 155D and points of attachment are all near 4D.

When full blown, the darker colored area along the petal margins is between 53A and 60B and widens to cover most of the petal surface. The reverse of the petals is near 155A and flushed with near 58A, Indian Lake Red.

Petaloids have the same color and texture as the inner petals. Their width and shape are quite variable. They may have streaks from the basal area, which are the same color as the basal area, up through the petal to the upper margin. They may be cleft where a wide streak from the point of attachment terminates, usually with part of a sterile anther attached. Occasionally, a very small piece of a petal has been seen adnate to one side of an anther, and a small petal seemingly growing out from one side of an anther.

REPRODUCTIVE ORGANS

Androecium: Stamens are arranged regularly around the outer edge of the receptacle, adjacent to the petals. They range in quantity from about 54 to about 75. The filaments vary in height from 6/32 to 14/32 inch. They appear somewhat translucent with the color at the base near 1C, a Chartreuse Green, and becoming near 47B, a medium red, approaching the anther. The color of the anthers is near 158C, a very pale yellow, and the surrounding pollen sacs are near 22A, Yellow Ochre.

Gynoecium: Pistils originate from within the center of the top of the receptacle and vary in quantity from about 24 to around 65 or more. Styles are thin and straight, varying from 3/32 to 8/32 inch long. The color is an Egyptian Buff, near 19C, from the base and a Cardinal Red, near 53A, toward the stigma. Stigmas are near 161D, a pale and dull yellow color. The stigmas are not receptive to pollen until after the pollen from that same flower is no longer virile.

Hips have not been observed.

PLANT

The plant of this new rose is upright growing, with good vigor and uniform branching. The height of the mature plant can reach up to 24 to 36 inches and the plant can grow to become 26 to 30 inches wide. When the flowers are borne singly the length of flowering stems is generally between 6 3/4 to 7 inches to the base of the peduncle. When part of a cluster, the length of the flowering stems varies from 1 5/8 to 3 inches, measured to the base of the peduncle. Diameters of flowering stems were found to be 5/32 inch near their base, tapering to 4/32 inch just below the peduncle.

Peduncles are strong and straight or may be curved slightly sunward. On singly borne flowers, the length of the peduncle varies from 1 4/32 to 1 17/32 inches and diameters are generally 5/32 inch right below the receptacle, tapering to 4/32 inch before connecting to the stem. Flowers borne in clusters have a shorter peduncle of about 29/32 inch with a diameter of about 3/32 inch. The surface of the peduncle is glossy right below the receptacle, becoming semi-glossy just above the connection to the stem. The color is a medium yellow-green, between 146C and 144B. Glands and stipitate glands are peppered over the surface. Peduncles dry and remain attached to the stem through succeeding bloom-cycles.

Foliage is pinnately compound, generally with five leaflets but occasionally there are seven or three. The length of the mature leaves ranges from 3 1/2 to 6 inches, regardless of the number of leaflets, with an average length of 4 1/2 inches.

Leaflets are broad-ovate to ovate and all with an acute apex. The average length of the terminal leaflets is 2 inches, ranging from $1\frac{25}{32}$ to $3\frac{14}{32}$ inches. Their average width is $1\frac{20}{32}$ inches, with measurements ranging from $1\frac{2}{32}$ to $1\frac{26}{32}$ inches and $1\frac{26}{32}$ inches being the most common width. The margin has a combination of simple and double serration and becomes increasingly shallow towards the base of the leaflet. There is a single gland at the tip of each serrate, and sometimes more glands along the margin near the juncture to the petiolule. The upper surface is matte to semi-glossy and glabrous. The main vein through the center of the leaflet and the primary lateral veins are recessed somewhat. Secondary lateral veins are barely recessed, becoming flush with the surface as they approach the margin. The under surface is matte with a leathery texture and glabrous appearance. The main vein protrudes entirely, primary lateral veins protrude somewhat, and the secondary lateral veins barely protrude.

Color of new foliage is a medium yellow-green, between 146A and 148A, and has a moderate flushing with a dark, grayed-purple, near 187A, with the areas near the margins near 146B and heavily flushed with the dark grayed-purple. The underside of the new foliage is near 146B and becomes completely flushed with near 187A. The anthocyanin coloring is absent from the mature leaflets. Their upper surface is a dark green, between 139A and 147A. Their under surface is near 147B.

Petioles appear a dark grayed-purple, near 187A, along the ridges and in the grooves on the upper side on young foliage. The color on the underside is near 144A and flushed lightly with near 187A. On mature foliage, the ridge of the upper side is the same dark green as the leaflet surface. The color in the groove is 144C, becoming lighter, between 160C and 154D, between the stipules. The underside is near 144C along the crest and becomes near 147A along the sides. The ridges are lined with stipitate glands, an occasional hair, and an occasional minute subulate appendage. The groove has variable amounts of glands and occasional hairs. The underside appears mostly glabrous, with a few glands visible toward the juncture with the rachis. Average petiole length is $1\frac{1}{4}$ inches, quite variable, from 1 to $1\frac{1}{2}$ inches. Petiole diameters are generally $\frac{3}{32}$ inch, regardless of length.

The rachis has the same coloring as the petiole, along the ridges, in the groove, and along the under surfaces, throughout its life cycle. Along the rachis the ridges are lined with glands, stipitate glands and occasional hairs. There are usually more stipitate glands at the juncture with the petiolules. Grooves appear to be glabrous, with no noticeable hairs or glands. The under surface has a few glands, stipitate glands and a prickle. Average rachis length is 1 inch, ranging from $\frac{24}{32}$ inch to $1\frac{15}{32}$ inches. Diameter varies from $\frac{2}{32}$ to $\frac{3}{32}$ inch.

Petiolules have the same coloring as the rachis throughout the life cycle of the leaf, with the exception that the groove of the petiolule on the mature leaf has lightened to near 146D, which is the color of the vein going into the leaflets. The texture of the petiolule is also the same as that of the rachis except with the absence of a prickle. Average and most common length of the petiolule to the terminal leaflet is $\frac{17}{32}$ inch, varying from $\frac{16}{32}$ to $\frac{22}{32}$ inch. Diameters are usually $\frac{2}{32}$ inch. The length of the petiolules to the basal leaflets ranges from $\frac{2}{32}$ to $\frac{4}{32}$ inch and is usually $\frac{1}{32}$ inch longer than the petiolules to the other side-leaflets.

Stipules are paired at the base of the petioles. The margins are lined mostly with stipitate glands but also with glands, serrates tipped with glands, and occasional hairs. They roll back tightly against the petiole. Length is quite variable, from $\frac{10}{32}$ to $\frac{17}{32}$ inch plus $\frac{2}{32}$ to $\frac{9}{32}$ inch tip angled outward from 40° to 75° from the petiole. The color on the upper surface is near 147A. The reverse is between 147A and 191B.

WOOD

The diameter of the main canes was measured at $\frac{20}{32}$ to $\frac{24}{32}$ inch. Primary laterals were from $\frac{15}{32}$ to $\frac{16}{32}$ inch in diameter. Secondary laterals had a diameter of $\frac{8}{32}$ to $\frac{10}{32}$ inch. Flowering stems were uniformly $\frac{5}{32}$ inch in diameter near their base and tapered to a diameter of $\frac{4}{32}$ inch just below the peduncle. Young canes are usually glabrous and gradually become scabrid and grow an increasing number of prickles. An occasional prickle that measured $\frac{7}{32}$ inch long was found on a flowering stem. Secondary laterals have none to two prickles per inch of stem that range in length from $\frac{9}{32}$ to $\frac{12}{32}$ inch. The quantity of prickles increases to the point where oldest canes may have fifty or more per inch, appearing to be almost completely covered with prickles but most of them are very short, from $\frac{1}{32}$ to $\frac{5}{32}$ inch in length. The prickles are straight or angled slightly downward and tapering quickly to a fine point. The color of the young prickles is near 181B, a medium red from the Greyed-Red Group. As they mature they become tan, near 165C, and on the old canes they are a dark gray, near 197A. On the underside of the rachis the color is a lighter and near translucent red, between 181D and 180C. Lenticels begin forming in streaks near the base of the older canes after 3 or 4 years. Their color is near 197A.

Variations: The above description is of plants and flowers as grown in the ground and in a container in Essex County, Mass., and in the spring in Arroyo Grande, Calif. Those same plants grown in California, both in the plastic-covered greenhouses and outdoors, during the summer months produced flowers with quite different shades of red. Their red coloring is more near Dutch Vermillion and Vermillion from the Red Groups 40 and 41, and becoming Scarlet Red, from the Red Group 43. Their colors showed none of the blue tonality noted in the flowers of the plants grown in Massachusetts and in the spring in California. All other aspects of the plant are the same. An image of flowers from plants grown inside a plastic covered greenhouse in Arroyo Grande, Calif., in the summer is included at the bottom right-hand corner of the enclosed patent image. In the bottom left-hand corner is an image of flowers from a plant grown in a glass-covered greenhouse in Millstone Township, N.J., showing colors that are somewhat between those of the other two images.

This new invention has been tested hardy to temperatures typical of zone 5. It has average resistance to black spot and above average resistance to powdery and downy mildews and rust.

The invention claimed is:

1. A new and distinct variety of rose plant is claimed, substantially as described and illustrated herein, having white flower petals edged with red, and that can blush entirely red in full sun, in a hybrid tea-form bloom, borne on a vigorous and upright plant.

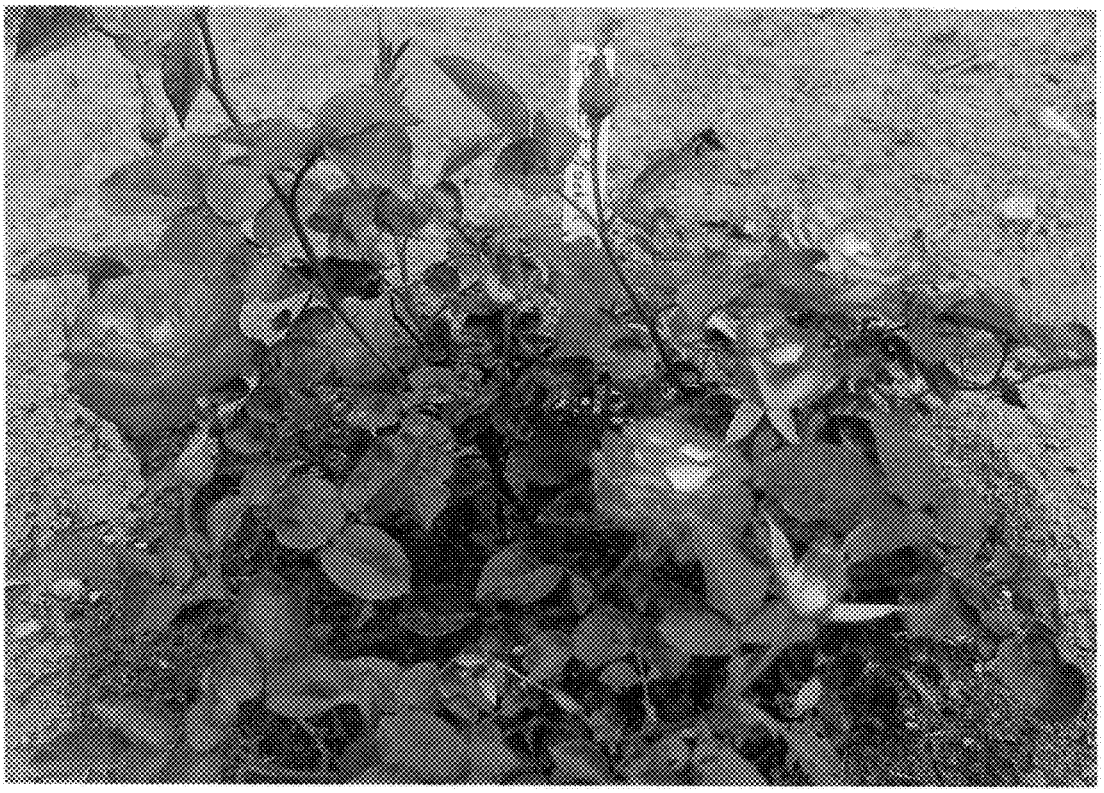
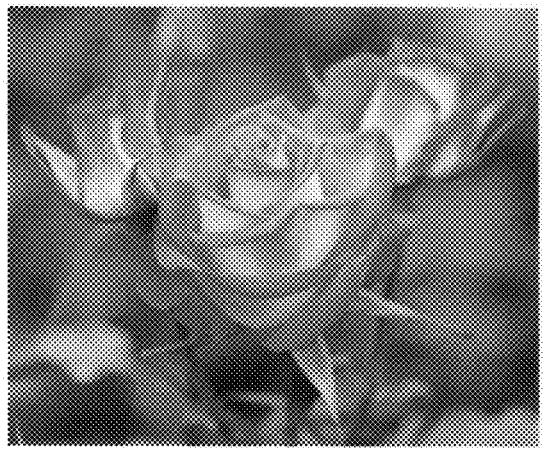
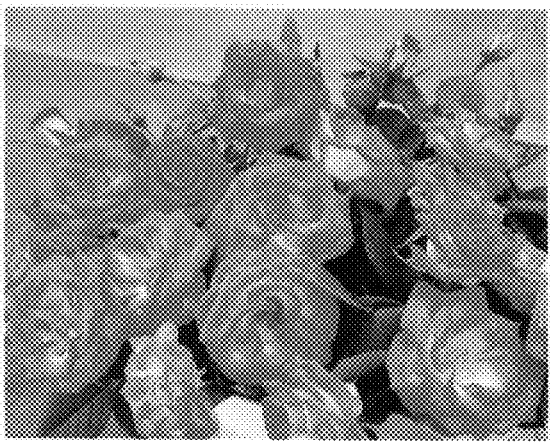

* * * * *